United States Patent
De Magalhaes

(10) Patent No.: US 11,865,182 B2
(45) Date of Patent: Jan. 9, 2024

(54) PRODUCT AND PROCESS FOR EMPLOYING GC7 (N1-GUANYL-1,7-DIAMINOHEPTANE) BASED ANTIGEN BINDING CONJUGATES IN CANCER THERAPY

(71) Applicant: Nzola De Magalhaes, Long Beach, CA (US)

(72) Inventor: Nzola De Magalhaes, Long Beach, CA (US)

( * ) Notice: Subject to any disclaimer, the term of this patent is extended or adjusted under 35 U.S.C. 154(b) by 503 days.

(21) Appl. No.: 16/764,859

(22) PCT Filed: Nov. 19, 2018

(86) PCT No.: PCT/US2018/061822
§ 371 (c)(1),
(2) Date: May 16, 2020

(87) PCT Pub. No.: WO2019/100005
PCT Pub. Date: May 23, 2019

(65) Prior Publication Data
US 2020/0338205 A1  Oct. 29, 2020

Related U.S. Application Data

(60) Provisional application No. 62/588,346, filed on Nov. 18, 2017.

(51) Int. Cl.
*A61K 31/155* (2006.01)
*A61K 47/68* (2017.01)
*G01N 33/574* (2006.01)

(52) U.S. Cl.
CPC ........ *A61K 47/6803* (2017.08); *A61K 31/155* (2013.01); *A61K 47/6853* (2017.08); *G01N 33/5748* (2013.01)

(58) Field of Classification Search
CPC .............. A61K 47/6803; A61K 31/155; A61K 47/6853; A61K 47/6849; G01N 33/5748; C07K 16/2863
USPC ....................................................... 424/178.1
See application file for complete search history.

(56) References Cited

U.S. PATENT DOCUMENTS

| | | |
|---|---|---|
| 2008/0311134 A1 | 12/2008 | Junutlual et al. |
| 2011/0070156 A1 | 3/2011 | Govindan et al. |
| 2012/0129910 A1 | 5/2012 | Thompson et al. |
| 2016/0348182 A1 | 12/2016 | Khosravifar et al. |
| 2020/0129639 A1* | 4/2020 | Levengood ........ A61K 47/6849 |
| 2020/0207859 A1* | 7/2020 | Molina ............ G01N 33/57407 |
| 2020/0338205 A1 | 10/2020 | De Magalhaes |

FOREIGN PATENT DOCUMENTS

| | | |
|---|---|---|
| CA | 3081925 A1 | 5/2019 |
| CN | 111565752 A | 8/2020 |
| EP | 3710054 A4 | 9/2020 |
| JP | 2021503454 A | 2/2021 |
| MX | 2020004530 A | 9/2020 |
| WO | 2004078940 A2 | 9/2004 |
| WO | 2009129220 A2 | 10/2009 |
| WO | 2010118224 A1 | 10/2010 |
| WO | 2015143382 A1 | 9/2015 |
| WO | 2017017133 A1 | 2/2017 |
| WO | 2017040342 A1 | 3/2017 |
| WO | 2019100005 A1 | 5/2019 |

OTHER PUBLICATIONS

Written Opinion of the International Search Authority dated May 2, 2019 issued on International Patent Application No. PCT/US2018/061822, filed Nov. 19, 2018 in the name of Nzola De Magalhaes.
International Search Report of the International Search Authority dated May 2, 2019 issued on International Patent Application No. PCT/US2018/061822, filed Nov. 19, 2018 in the name of Nzola De Magalhaes.
Xue Fei et al.: "eIF5A2 is an alternative pathway for cell proliferation in cetuximab-treated epithelial hepatocellular carcinoma", Am J Transl Res, Jan. 1, 2016 (Jan. 1, 2016), pp. 4670-4681, XP055816569, Retrieved from the Internet: URL:https://www.ncbi.nlm.nih.gov/pmc/articles/PMC5126312/pdf/ajtr0008-4670.pdf [retrieved on Jun. 22, 2021].
European Search Report dated Jul. 9, 2021 on a EP No. EP18879090, filed Dec. 24, 2020.
Notice of Reasons for Refusal dated Nov. 10, 2022, on a Japanese Patent Application No. 2020-526555, filed May 1, 2020. English abstract attached.

* cited by examiner

*Primary Examiner* — Yan Xiao

(74) *Attorney, Agent, or Firm* — Franklin & Associates International Inc; Matthew F. Lambrinos

(57) ABSTRACT

The present invention generally relates to methods of theranostic compounds and their use to selectively kill a class of cancer cells. Methods and means related to the treatment of cancers which overexpress the KRAS gene and/or eIF5A gene with inhibitors of eIF5A hypusination, including G7, are disclosed.

5 Claims, 12 Drawing Sheets

BxPC-3 Cell Line Drug Response

| 1 | Control/ no drug | 7  | CET DTME 25 | 13 | CET SPDP 25 | 19 | CET EDC 13 |
|---|---|---|---|---|---|---|---|
| 2 | CET-Dye 25 | 8  | CET DTME 50 | 14 | CET SPDP 50 | 20 | CET EDC 25 |
| 3 | CET-Dye 75 | 9  | CET DTME 75 | 15 | CET SPDP 75 | 21 | CET EDC 50 |
| 4 | CEA-Dye 25 | 10 | CEA DTME 25 | 16 | CEA SPDP 25 | 22 | CEA EDC 13 |
| 5 | CEA-Dye 75 | 11 | CEA DTME 50 | 17 | CEA SPDP 50 | 23 | CEA EDC 25 |
| 6 | GC7 25     | 12 | CEA DTME 75 | 18 | CEA SPDP 75 | 24 | CEA EDC 50 |

FG Cell Line Drug Response

| 1 | Control/ no drug | 7 | CET DTME 25 | 13 | CET SPDP 25 | 19 | CET EDC 13 |
|---|---|---|---|---|---|---|---|
| 2 | CET-Dye 25 | 8 | CET DTME 50 | 14 | CET SPDP 50 | 20 | CET EDC 25 |
| 3 | CET-Dye 75 | 9 | CET DTME 75 | 15 | CET SPDP 75 | 21 | CET EDC 50 |
| 4 | CEA-Dye 25 | 10 | CEA DTME 25 | 16 | CEA SPDP 25 | 22 | CEA EDC 13 |
| 5 | CEA-Dye 75 | 11 | CEA DTME 50 | 17 | CEA SPDP 50 | 23 | CEA EDC 25 |
| 6 | GC7 25 | 12 | CEA DTME 75 | 18 | CEA SPDP 75 | 24 | CEA EDC 50 |

Panc-1 Cell Line Drug Response

| 1 | Control/ no drug | 7 | CET DTME 25 | 13 | CET SPDP 25 | 19 | CET EDC 13 |
|---|---|---|---|---|---|---|---|
| 2 | CET-Dye 25 | 8 | CET DTME 50 | 14 | CET SPDP 50 | 20 | CET EDC 25 |
| 3 | CET-Dye 75 | 9 | CET DTME 75 | 15 | CET SPDP 75 | 21 | CET EDC 50 |
| 4 | CEA-Dye 25 | 10 | CEA DTME 25 | 16 | CEA SPDP 25 | 22 | CEA EDC 13 |
| 5 | CEA-Dye 75 | 11 | CEA DTME 50 | 17 | CEA SPDP 50 | 23 | CEA EDC 25 |
| 6 | GC7 25 | 12 | CEA DTME 75 | 18 | CEA SPDP 75 | 24 | CEA EDC 50 |

779E Cell Line Drug Response

| 1 | Control/ no drug | 7 | CET DTME 25 | 13 | CET SPDP 25 | 19 | CET EDC 13 |
|---|---|---|---|---|---|---|---|
| 2 | CET-Dye 25 | 8 | CET DTME 50 | 14 | CET SPDP 50 | 20 | CET EDC 25 |
| 3 | CET-Dye 75 | 9 | CET DTME 75 | 15 | CET SPDP 75 | 21 | CET EDC 50 |
| 4 | CEA-Dye 25 | 10 | CEA DTME 25 | 16 | CEA SPDP 25 | 22 | CEA EDC 13 |
| 5 | CEA-Dye 75 | 11 | CEA DTME 50 | 17 | CEA SPDP 50 | 23 | CEA EDC 25 |
| 6 | GC7 25 | 12 | CEA DTME 75 | 18 | CEA SPDP 75 | 24 | CEA EDC 50 |

PRODUCT AND PROCESS FOR EMPLOYING GC7 (N1-GUANYL-1,7-DIAMINOHEPTANE) BASED ANTIGEN BINDING CONJUGATES IN CANCER THERAPY

CROSS-REFERENCE TO RELATED APPLICATIONS

This application is the National Stage of International PCT Application No. PCT/US2018/061822, filed 19 Nov. 2018, which claims the benefit of the provisional application entitled GC7 (N1-GUANYL-1,7-DIAMINOHEPTANE) BASED ANTIGEN BINDING CONJUGATES with U.S. Application No. 62/588,346 filed on Nov. 18, 2017.

The present invention relates to the fields of medicinal chemistry and pharmaceutical chemistry. In particular, the present invention relates to theranostic compounds containing antibodies, antibody fragments or peptides conjugated to toxins, with therapeutic and diagnostic properties against cancer and other diseases and disorders.

BACKGROUND OF THE INVENTION

Although the combined death rate for all cancers has declined in the past 10 years, the death rate for pancreatic cancer has increased by 0.4% each year. Even after conventional treatment comprising of conventional chemotherapy, radiation and surgery, cancer recurrence is high. The 5-year survival rate after the conventional methods of treatment is only 1-5%. The high recurrence of pancreatic cancer is due in part to resistance associated with mutations in the KRAS gene. Ninety-five percent (95%) of pancreatic cancers are associated with pre-existing mutations in the KRAS gene. However, repeated treatment sessions and/or the incomplete killing of tumors due to poor tumor selectivity and cytotoxic efficiency of conventional therapies have also been linked to therapeutic resistance mutations in the KRAS gene.

Recent evidence indicates that mutational activation of KRas up-regulates eukaryotic translation initiation factor 5A (eIF5A), a component of the cellular translational machinery that is critical for the progression of human pancreatic ductal adenocarcinoma (PDAC). EIF5A may be responsible for fine-tuning the expression of a set of proteins to drive PDAC cell migration and metastasis, and thus may play a key role in the pathogenesis of PDAC. EIF5A expression in PDAC cells is regulated by a unique pathway involving the hypusination of the eIF5A proteins. Hypusination is a distinct posttranslational modification process that activates the eIF5A protein through hydroxylation of the amino acid hypusine, which is mediated by two enzymes, deoxyhypusine synthase (DHS) and deoxyhypusine hydroxylase (DOHH).

Inhibiting the hypusination pathway of eIF5A leads to cell death, inhibition of metastasis and significant reduction of KRas expression in KRAS-mutated and wild-type human PDAC cell lines in vitro and in vivo. Thus, eIF5A hypusination pathway regulates KRas protein expression (as well as being regulated by KRas expression). In addition, inhibitors of DHS and DOHH blocked eIF5A hypusination and activity causing the efficient killing of chemotherapy resistant PDAC cells in vitro; suggesting the potential use of these inhibitors as anti-pancreatic cancer drugs in vivo.

Separately, it has been observed that KRAS-driven pancreatic cancers become sensitive to therapeutic drugs when hypusination is inhibited or eIF5A is knocked down.

Pharmacological inhibition of eIF5A hypusination via GC7 based antigen binding conjugates may significantly repress tumor growth and metastasis in vivo in KRAS driven tumors. Although significant cytotoxicity is observed in vitro after GC7 administration, results in vivo have been mixed. It is suspected that the systemic distribution of the drug to all cells lowers the amount of drug delivered to tumor cells, thereby reducing its effectiveness.

Immunoconjugates or antigen binding conjugates are molecules that contain an antigen binding entity, such as an antibody, peptide, or antigen binding fragment, linked to a cytotoxic agent via crosslinkers. In cancer and angiogenic disorders, the antigen binding entity in the conjugate is used to deliver the cytotoxic agent or drug load or drug moiety specifically to the cells containing the corresponding antigen, minimizing toxicity to untargeted normal and healthy cells.

Currently, there are no approved GC7 based immunoconjugates, such as antibody-drug conjugates (commonly referred as ADCs) and peptide-drug conjugates (commonly referred as PDCs) for safe use in therapy of diseases, such as cancer, immunological and infective diseases, and GC7 has yet to be described in conjugation to an antibody, peptide or antigen binding fragment.

Therefore, there is an urgent need for a curative treatment to improve the overall survival rate of patients afflicted by this disease. Development of an effective therapeutic strategy that not only overcome drug and radiation resistance but also inhibit tumor recurrence, could help decrease the mortality rate and improve the quality of life of pancreatic cancer patients.

SUMMARY OF THE INVENTION

According to embodiments of the present invention, the present invention is directed to a method of treating cancerous cells, wherein said method comprises of administering to a population of cancer cells, an effective amount of an antibody drug conjugate (ADC) in the form of n(m(I)-L)-Ab-(L-(D)m)n, wherein Ab represents a molecule from the group consisting of an antibody, a peptide, a polypeptide, a protein, and antigen binding fragment; D represents a drug moiety; I represents an imaging agent; L represents a linker; m represents an integer in the range of 1 to 8; and n represents an integer in the range of 1 to 10.

According to embodiments of the present invention, D is an inhibitor of eukaryotic initiation factor 5A (eIF5A). According to other embodiments of the present invention, the eIF5A inhibitor is a form of N1-guanyl-1,7-diaminoheptane (GC7).

According to embodiments of the present invention, the ADC is combined with other therapeutic agents in the treatment of cancer cells.

According to an alternate embodiment of the current invention, the method comprises of a method for diagnosing and treating cancer cells, said method comprising of (a) receiving a cancer sample from the subject; (b) testing the cancer sample for an abnormality of the KRas; and (c) administering antibody drug conjugate (ADC) in the form of: n(m(I)-L)-Ab-(L-(D)m)n, wherein Ab represents a molecule from the group consisting of an antibody, a peptide, a polypeptide, a protein, and antigen binding fragment; D represents a drug moiety; I represents an imaging agent; L represents a linker; m represents an integer in the range of 1 to 8; and n represents an integer in the range of 1 to 10.

According to the alternate embodiment of the current invention, the drug moiety is an inhibitor of hypusination of the eukaryotic initiation factor 5A (eIF5A). In some embodiments, the hypusination inhibitor is a form of N1-guanyl-1,7-diaminoheptane (GC7).

According to a further embodiment of the current invention, a method of targeting cancer cells comprising of using a theranostic antibody drug conjugate (ADC), wherein said ADC comprises of a drug that inhibits hypusination of eukaryotic initiation factor 5A (eIF5A).

According to a further embodiment of the current invention, the theranostic antibody drug conjugate comprises of an inhibitor of hypusination of eukaryotic initiation factor 5A (eIF5A). According to some embodiment, the hypusination inhibitor is the form of N1-guanyl-1,7-diaminoheptane (GC7), inhibitors of deoxyhypusine synthase (DHS), or inhibitors deoxyhypusine hydroxylase (DOHH). According to other embodiments, the theranostic antibody drug conjugate comprises of one or more hypusination inhibitors such as GC7, inhibitors of DHS, or inhibitors of DOHH.

According to an even further embodiment of the current invention, a method for a targeted delivery of drug for the treatment of cancer cells comprising of (i) determining a cell-surface protein that is overexpressed in the cancerous cells and (ii) designing a conjugate in the form of n(m(I)-L)-Ab-(L-(D)m)n wherein Ab represents a molecule from the group consisting of an antibody, a peptide, a polypeptide, a protein, and antigen binding fragment; D represents a drug moiety; I represents an imaging agent; L represents a linker; m represents an integer in the range of 1 to 8; and n represents an integer in the range of 1 to 10.

According to the even further embodiment of the current invention, the method comprises of designing an ADC conjugate that overexpress KRas protein. In some embodiments, the drug is an inhibitor of eIF5A, and in further embodiments, the drug is a form of N1-guanyl-1,7-diaminoheptane (GC7).

According to the even further embodiments of the current invention, the method is used upon mammals, and in some embodiments, the method is used in humans.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 6 shows the results of a cell viability assay and drug response after treatment of BxPC-3 cells with the ADCs of the present invention with G7 as the drug moiety, compared to treatment with CEA and Cetuximab antibodies. BxPC-3 are a cell line that exhibit a high expression of eIF5a.

FIG. 7 shows the results of a cell viability assay and drug response after treatment of FG cells with the ADCs of the present invention with G7 as the drug moiety, compared to treatment with CEA and Cetuximab antibodies. FG cells expressly a relatively normal level of eIF5a.

FIG. 8 shows the results of a cell viability assay and drug response after treatment of Panc-1 cells with the ADCs of the present invention with G7 as the drug moiety, compared to treatment with CEA and Cetuximab antibodies. Panc-1 cells expressly a relatively normal level of eIF5a. FIG. 8e graphically represents the control data.

FIG. 9 shows the results of a cell viability assay and drug response after treatment of 779E cells with the ADCs of the present invention with G7 as the drug moiety, compared to treatment with CEA and Cetuximab antibodies. 779E cells expressly a relatively normal level of eIF5a.

DETAILED DESCRIPTION OF THE INVENTION

Figure 1A:
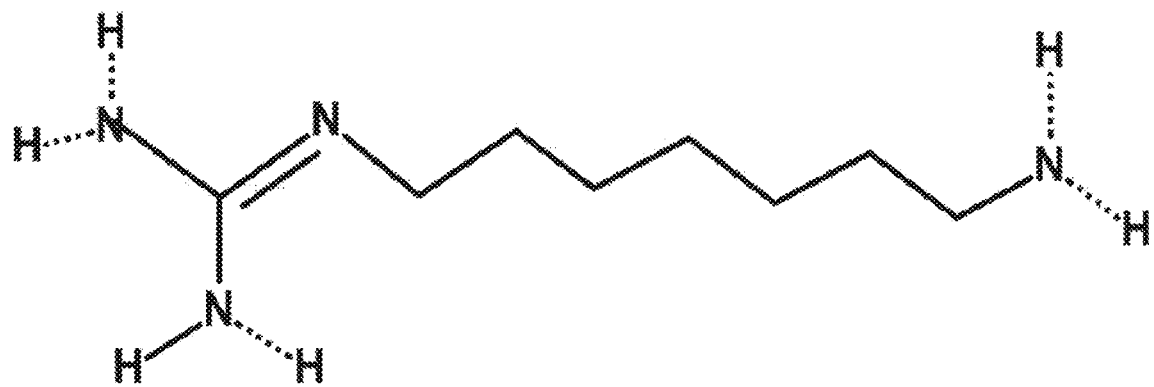
FIG. 1a provides the chemical structure of the GC7 (N1-guanyl-1,7-diaminoheptane) molecule while FIG. 1b provides the chemical structure of the salt form of GC7, namely 1-(7-ammonioheptyl)guanidinium sulfate.

In general, the current invention comprises of conjugate compounds and methods of use of such conjugate compounds for the selective detection and treatment of diseases such as cancer. The conjugate compound is generally of the formula: $_n(_m(I)\text{-L})\text{-Ab-}(L\text{-}(D)_m)_n$ or a pharmaceutically acceptable salt thereof; wherein Ab is an antibody, a peptide, a polypeptide/protein or an antigen binding fragment thereof; L is a linker; D is a drug moiety; I is an imaging agent; m is an integer from 1 to 8; and n is an integer from 1 to 10. The Ab (or mAB) is a peptide-based moiety that is used to adhere to a target site. Once the Ah is hound to its target site (e.g. a cell surface receptor on a cancerous cell), an imaging moiety, affixed to the Ab moiety via a linker, can guide in the identification and localization of the target site. Separately, the Ab is also bound to a drug moiety via a linker. This allows for the delivery of treatment to the target site. Accordingly, the current invention allows for the detection and treatment of a pathology at a molecular level.

In the preferred embodiment, the invention targets eukaryotic initiation factor 5A (eIF5a) in mammals, namely humans, because this protein is overexpressed in PDAC cells due to mutations in KRAS. Accordingly, suitable drug moieties in the claimed invention include inhibitors of eIF5a such as the sub-class of inhibitors of hypusination.

Overexpression can be defined in multiple ways, but most essence, it is defined as the level of gene expression above normal. It has been known that the gene expression patterns are complexly different between normal and cancerous cells. Accordingly, normal expression of gene is defined as the level of protein that does not induce a noticeable change whereas overexpression of a gene is defined as such level that contributes to phenotypic variability. There are primarily two means by which a gene can be overexpressed. In one simplified model, a gene is overexpressed due to allosteric reactions. The other is due to gene duplication.

The present invention provides GC7 based antigen binding or biomarker driven conjugates, and methods for making, preparing, synthesizing, conjugating, and purifying, the conjugates and any intermediates produced during the application of these methods, using antigen binding entities, linkers, imaging agents, and GC7, GC7 analogues or a pharmaceutically acceptable salt thereof. The compounds of the present invention may be used as therapeutics and in the diagnosis, prevention and/or treatment of diseases such as cancer, immunological and infective diseases. Currently, there are no approved GC7 based antibody-drug conjugates (commonly referred as ADCs) and peptide-drug conjugates commonly referred as PDCs) for safe use in treatment of diseases.

The benefits of the present invention conjugates include but are not limited to targeting tumor cells leaving normal tissue intact, increasing sensitivity of KRAS mutated tumor cells to chemotherapy, and capability to employ three therapeutic approaches. The present invention conjugates can elicit cytotoxicity in-vitro and in-vivo in tumor cells via photo therapy, antibody therapy, and drug therapy in tumor cells that overexpress eIF5A protein via the toxin moiety, GC7.

According to embodiments of the present invention, the antibody (Ab), the cell-binding agent, according to the present invention can be, without limitation, a monoclonal antibody, a chimeric antibody, a humanized antibody, a human engineered antibody, a human antibody, or a recombinant human antibody, camelid antibodies, anti-idiotypic antibodies, a cysteine or other amino acid substituted antibody, a domain antibody, a polyclonal antibody, a single chain antibody (scFv), or an antibody fragment thereof, a lymphokine, a hormone, a vitamin, a growth factor, a colony stimulating factor, or a nutrient-transport molecule. In some aspects of the invention, the antibody is a non-internalizing antibody, an internalizing antibody and/or a neutralizing antibody.

The antibodies can be of any isotype/class (e.g., IgM, IgA, IgG, IgD, IgE and IgY), or subclass (e.g., IgG2, IgG2, IgG3, IgG4, IgA1 and IgA2).

The antibodies in certain embodiments of the present invention include, but are not limited to, anti-CEA, anti-CA 19-9, anti-EGFR, anti-folate receptor antibody, Cetuximab, panitumumab, Trastuzumab, pertuzumab, obinutuzumab, brentuximab, rituximab, or ofatumumab.

According to embodiments of the current invention, the antibodies, antibody fragments (e.g., antigen binding fragments) or functional equivalents of the present disclosure may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

According to embodiments of the current invention, the peptide, polypeptide or protein according to the present invention can be, without limitation, natural L or D or both configuration type-amino acids and artificial peptides.

According to embodiments of the current invention, the linker (L) according to the present invention can be, without limitation, a cleavable linker, a non-cleavable linker, a hydrophilic linker, a procharged linker, a dicarboxylic acid based linker, a homobifunctional linker, a heterobifunctional linker, a thiol reactive crosslinker, a carboxyl-to-amine reactive crosslinker, an aldehyde reactive crosslinker, a photo-reactive crosslinker, a hydroxyl reactive crosslinker or a azide reactive crosslinker, in addition to other types of linkers. In one aspect, the linker may be hetrobifunctional zero-length EDC (1-ethyl-3-(3-dimethylaminopropyl) carbodiimide hydrochloride) crosslinker. In another aspect, the cleavable linker may be heterobifunctional SPDP (N-succinimidyl 3-(2-pyridyldithio) propionate) crosslinker; In another aspect, the cleavable linker may be homobifunctional DTME (Dithiobismaleimidoethane).

The linkers in certain embodiments of the present invention include, but are not limited to, heterobifunctional zero-length EDC (1-ethyl-3-(3-dimethylaminopropyl)carbodiimide hydrochloride) crosslinker. In another aspect, the cleavable linker may be heterobifunctional SPDP (N-succinimidyl 3-(2-pyridyldithio) propionate) crosslinker; In another aspect, the cleavable linker may be homobifunctional DTME (Dithiobismaleimidoethane).

According to embodiments of the current invention, the imaging agent (I) according to the present invention can be, without limitation, a detectable compound or composition, such as a fluorophore or a PET (Positron Emission Tomography) tracer, a SPECT (Single-Photon Emission Computed Tomography) tracer, or an MRI (Magnetic Resonance Imaging) tracer. The imaging agent may be detectable by itself (e.g., radioisotope tracers or fluorescent dyes) or, in the case of an enzymatic agent, may catalyze chemical alteration of a substrate compound or composition that is detectable. Radionuclides that can serve as detectable compounds include, for example, 1-131, 1-123, 1-125, Y-90, Re-188, Re-186, At-211, Cu-67, Bi-212, and Pd-109. The imaging agent may also be a therapeutic imaging agent (e.g. a photosensitive dye) or it might also be substituted for a non-detectable entity such as a toxin or drug moiety. In summary, the imaging agent (I) can be a therapeutic, non-therapeutic or a diagnostic agent.

The imaging agents in certain embodiments of the present invention include, but are not limited to M-tetrahydroxyphenyl Chlorine (mTHPC), a phthalocyanine based dye, such as 700 Dx, Lutetium Texaphyrin (PCI-0123), and fluorescent dyes such as DYLIGHT 550 NHS, DYLIGHT 650 NHS, and DYLIGHT 800 NHS.

According to alternative embodiments of the current invention, the antibody or peptide drug conjugates of any of the preceding embodiments can be in combination with another therapeutic agent.

According to alternative embodiments of the current invention, any cell-binding agent is used to target cells, such as tumor cells, virus infected cells, microorganism infected cells, parasite infected cells, autoimmune cells, activated cells, myeloid cells, activated T-cells, B cells, or melanocytes. Other targets includes cells expressing CEA, eIF5A, or Her-2 antigens; Her-3 antigens; or cells expressing insulin growth factor receptors, epidermal growth factor receptors, and folate receptors.

Another object of the present invention is a pharmaceutical composition comprising the antibody or peptide drug conjugates of any of the preceding embodiments and a pharmaceutically acceptable carrier, vesicle or excipient.

The conjugate, according to the present invention, can be prepared with conventional methods known in the field. Any other suitable method can be conveniently used. The efficacy of the conjugates can be tested in-vivo using laboratory animal models, and in-vitro on selected cell lines overexpressing the antigen recognized by the conjugate's antibody, peptide or antigen binding fragment and or positive for eIF5A.

Embodiments of the present invention may take the form of pharmaceutically acceptable salts, e.g., a salt of a compound that is pharmaceutically acceptable and that possesses the desired pharmacological activity of the parent compound. Example illustration of the salt form may be: (1) acid addition salts, formed with inorganic acids such as hydrochloric acid, hydrobromic acid, sulfuric acid, nitric acid, phosphoric acid, and the like; or formed with organic acids such as acetic acid, butyric acid, propionic acid, hexanoic acid, cyclopentanepropionic acid, glycolic acid, pyruvic acid, lactic acid, valeric acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hy-droxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like, made by conventional chemical means; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucanine and the like, made by conventional chemical means.

To illustrate the structures and methods of the current invention along with data demonstrating the efficacy of the current invention, the following figures are disclosed.

Figure 1B:
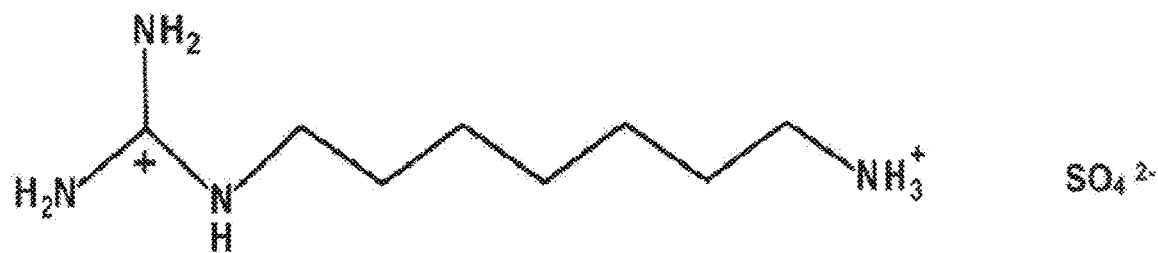
FIG. 1 illustrates the chemical forms of a hypusination inhibitors.

FIG. 1 illustrates the chemical forms of a hypusination inhibitor. FIG. 1a provides for the chemical structure of GC7 while FIG. 1b provides for the chemical structure of GC7 in the form of the salt, 1-(7-ammonioheptyl)guanidinium sulfate. GC7 targets and inhibits deoxyhypusine synthase (DHS) by competitively binding to the active site of DHS. This competitive binding thwarts the first step in the post-translational conversion of a single lysine to hypusine in eIF5A.

Figure 2:
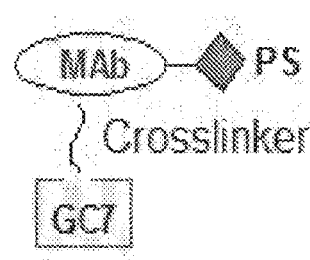
FIG. 2 shows a graphic depiction of the GC7 based ADC (Antibody Drug Conjugate) construct design.
Figure 3:
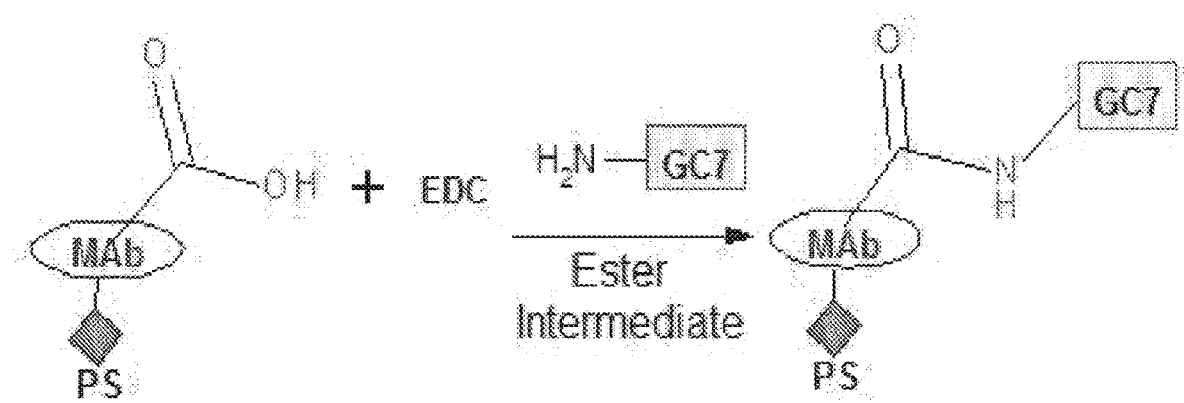
FIG. 3 shows a graphic depiction of GC7 based ADC generated via the EDC (Carbodiimide crosslinker) coupling reaction.
Figure 4:
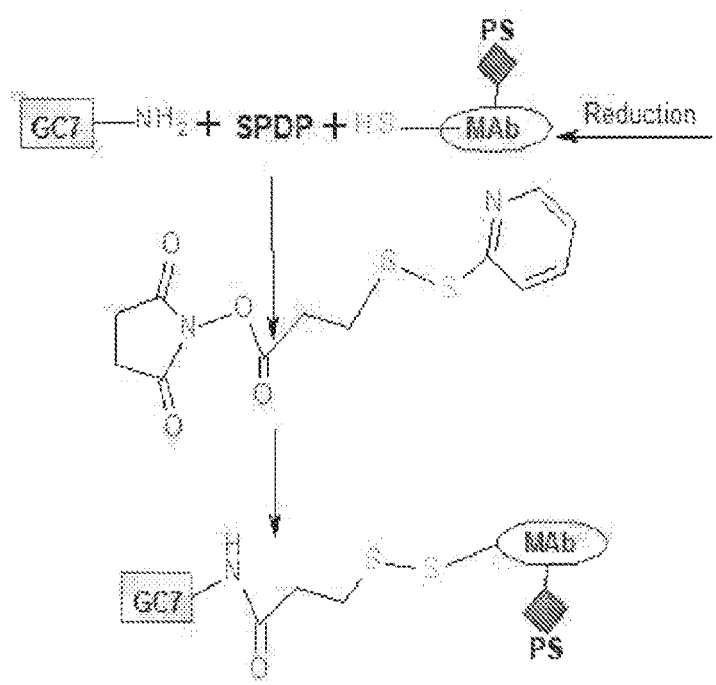
FIG. 4 shows a graphic depiction of GC7 based ADC generated via the Maleimide chemistry reaction using the cleavable heterobifunctional SPDP (N-succinimidyl 3-(2-pyridyldithio) propionate) crosslinker.
Figure 5:
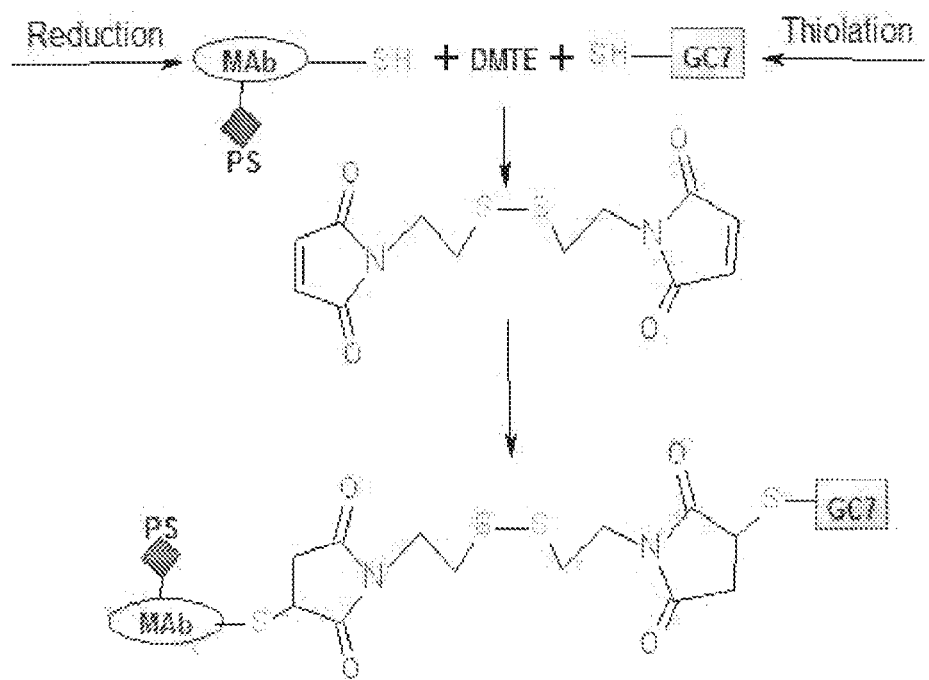
FIG. 5 shows a graphic depiction of GC7 based ADC generated via the Maleimide chemistry reaction using the cleavable homobifunctional DTME (Dithiobismaleimidoethane) crosslinker.
Figures 6A, 6B:
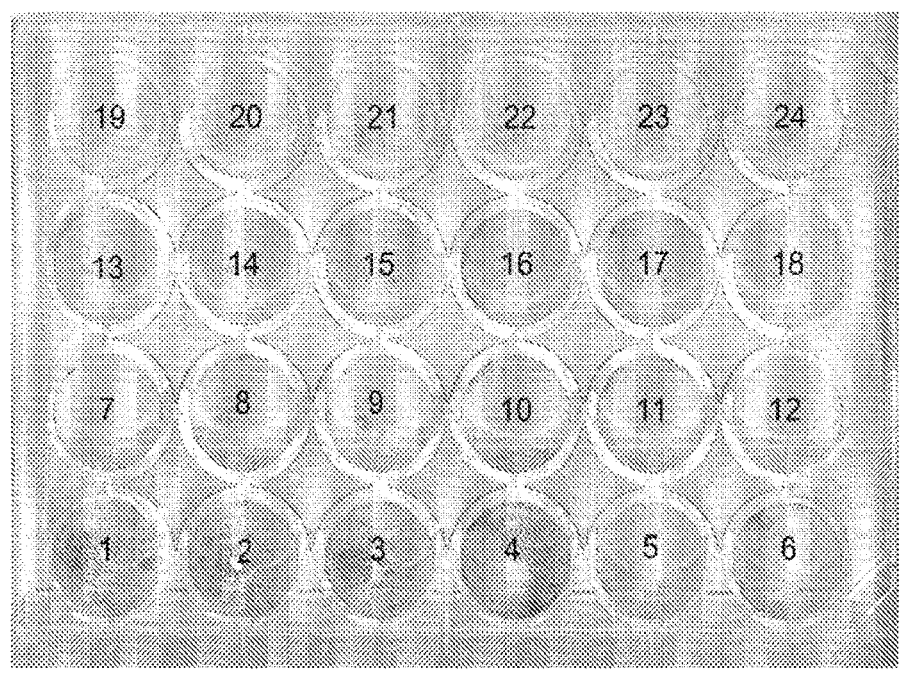
FIG. 6a shows the allocation of control and treatment groups.
FIG. 6b shows the raw data after treatment with Crystal Violet.
Figure 6C:
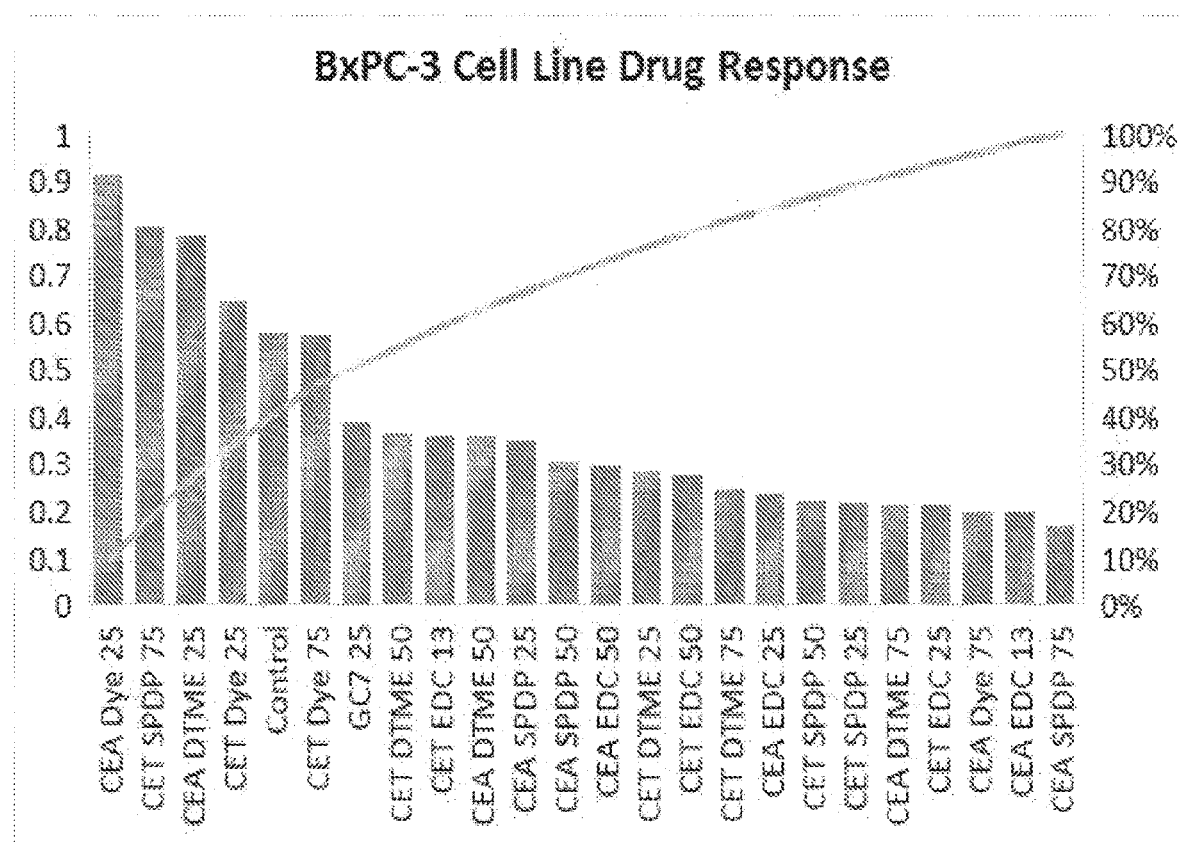
FIG. 6c graphically represents the control data.
Figures 7A, 7B:
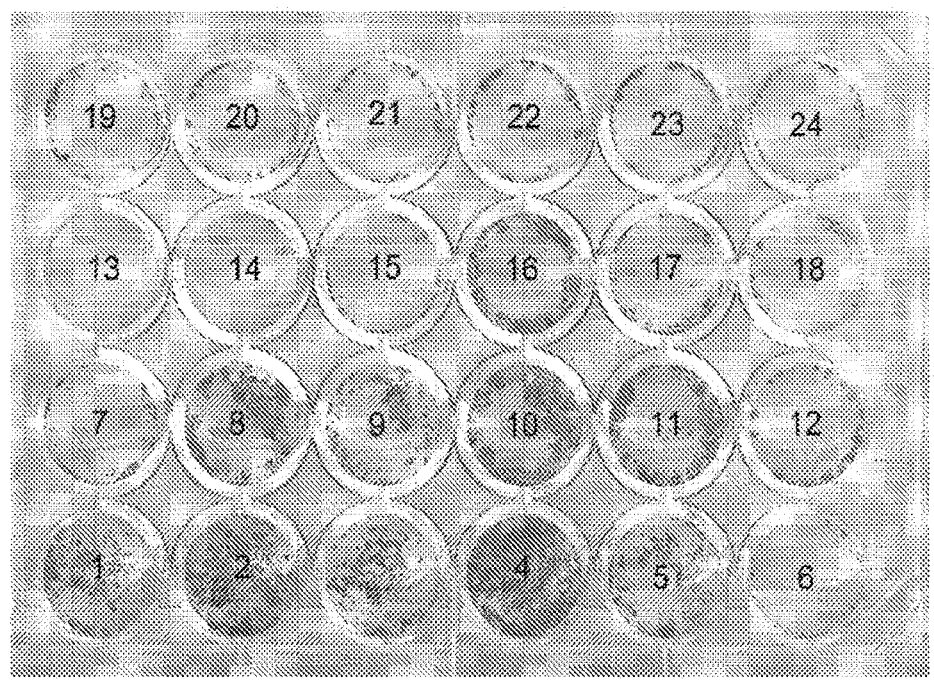
FIG. 7a shows the allocation of control and treatment groups.
FIG. 7b shows the raw data after treatment with Crystal Violet.
Figure 7C:
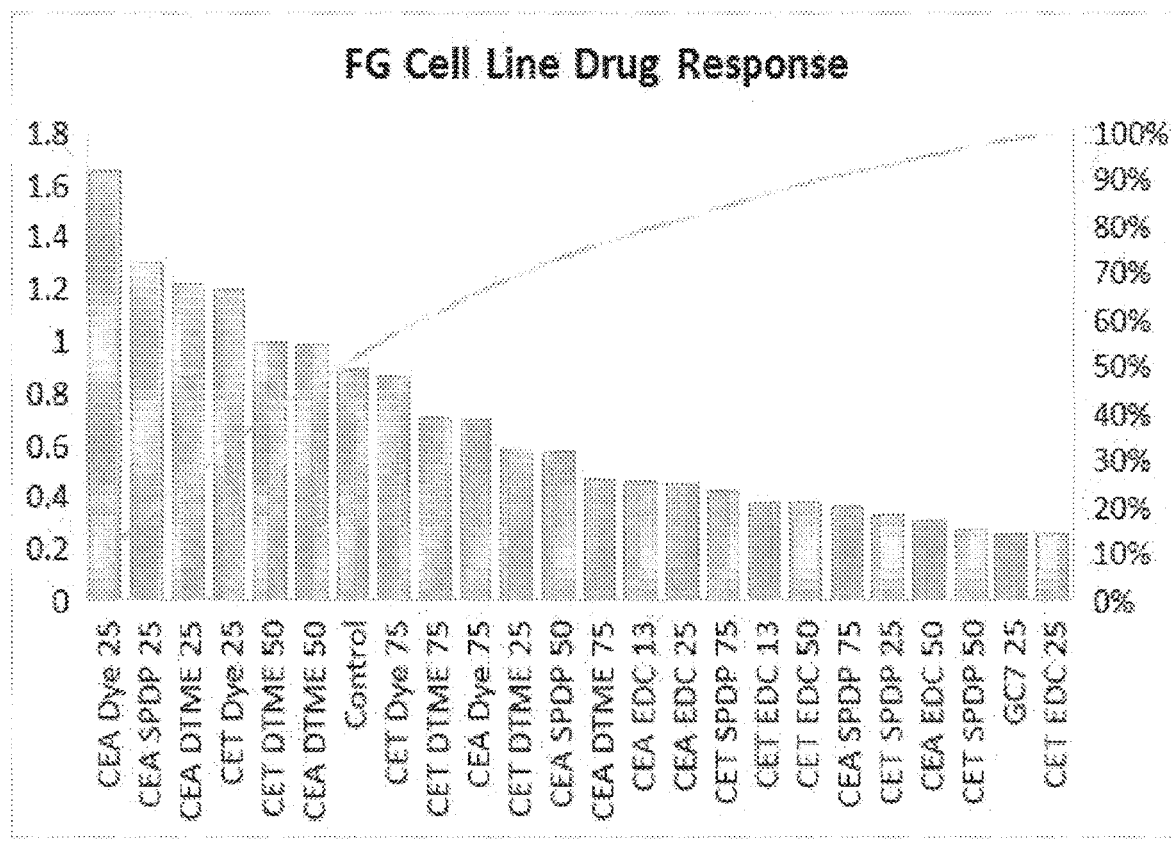
FIG. 7c graphically represents the control data.
Figures 8A, 8B:
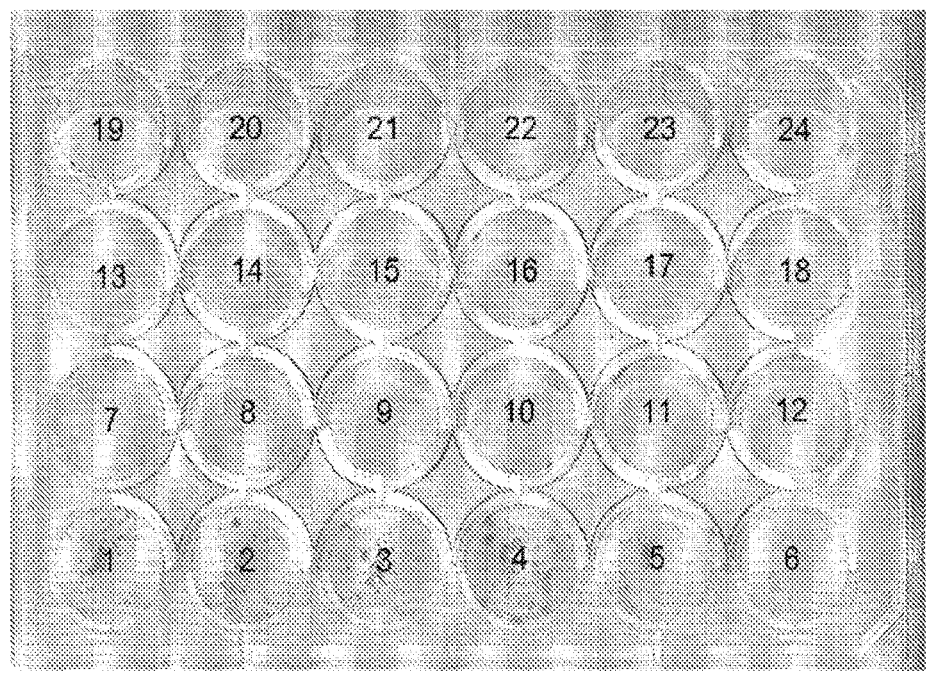
FIG. 8a shows the allocation of control and treatment groups.
FIG. 8b shows the raw data after treatment with Crystal Violet.
Figure 8C:
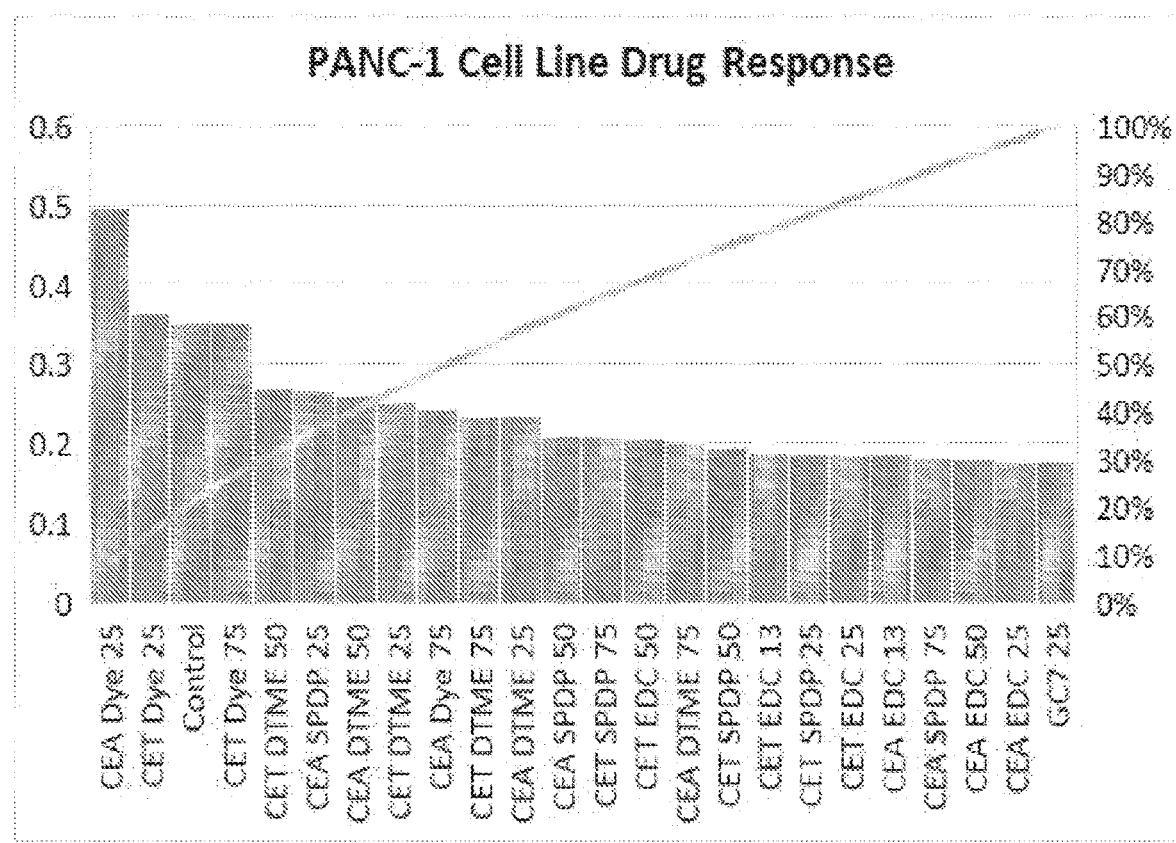
Figures 9A, 9B:
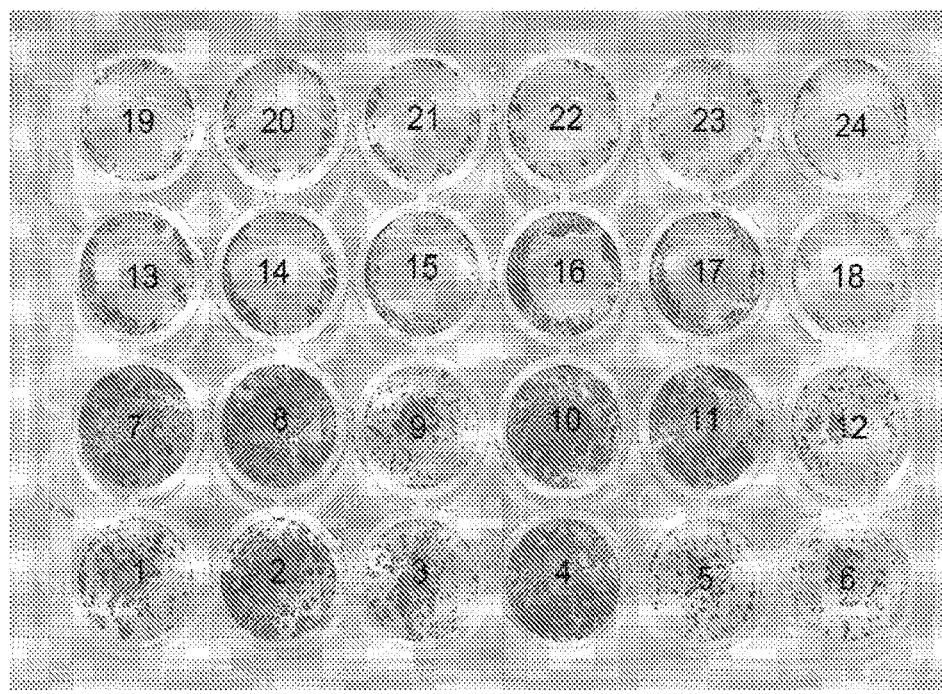
FIG. 9a shows the allocation of control and treatment groups.
FIG. 9b shows the raw data after treatment with Crystal Violet, FIG. 9e graphically represents the control data.
Figure 9C:
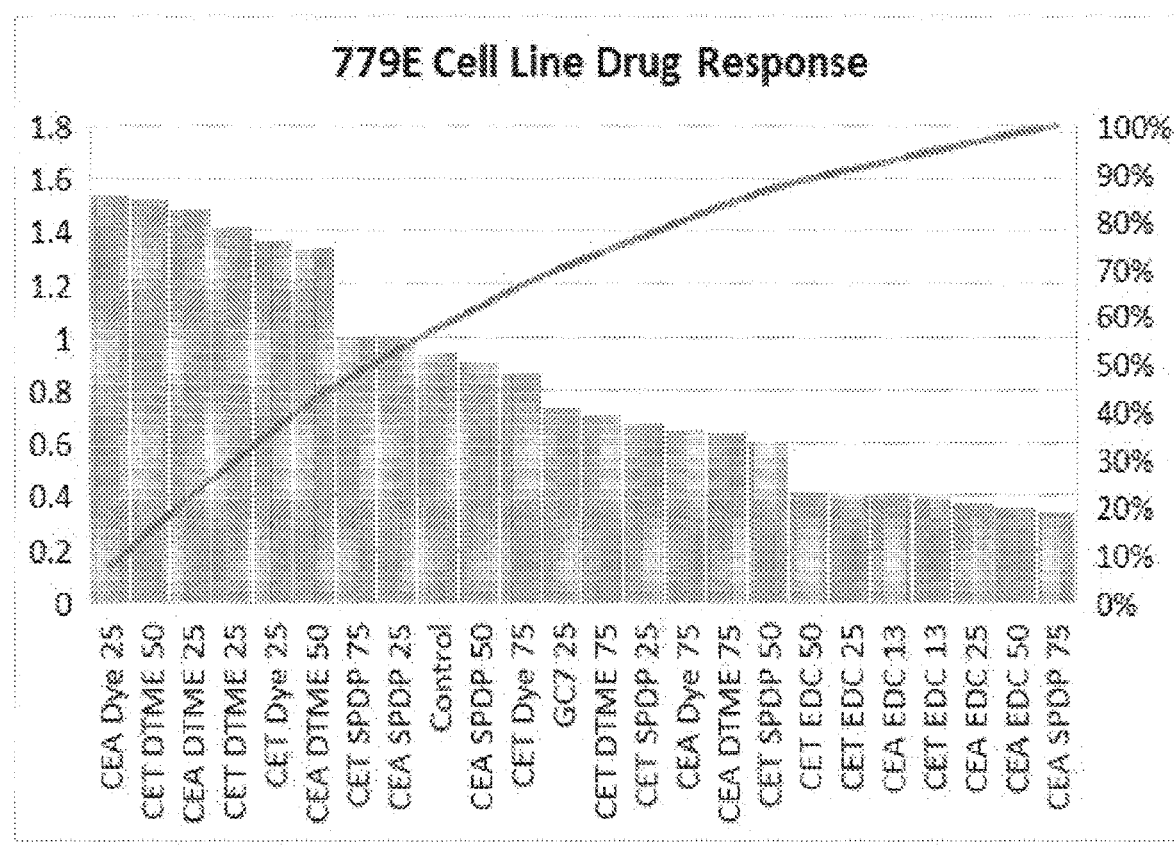

Specific embodiments of the present GC7 immunoconjugates as illustrated in FIGS. 2, 3, 4 and 5. In these figures, PS representatives a photosensitizer and Mab represents antibodies, but can be any molecule from the group consisting of an antibody, a peptide, a polypeptide, a protein, and antigen binding fragment. In the illustration GC7 can be substituted with any drug moiety. FIG. 2 shows a graphic depiction of the general GC7-based ADC construct design. The illustrated embodiments of the GC-based ADC contain near-infrared fluorescently tagged GC7 attached to antibodies for EGFR (Epithelial Growth Factor Receptor) or CEA (Carcinoembryonic antigen) since both EGFR and CEA are overexpressed in PDAC tumors, with and without a cleavable crosslinker, using three different established conjugation chemistries. FIG. 3 shows a reaction with EDC (Carbodiimide crosslinker) which results in no addition of the crosslinker in the final ADC product. FIG. 4 shows another approach using a pyridyl disulfide reaction to conjugate the antibody with GC7 using a cleavable heterofunctional crosslinker, SPDP. FIG. 5 shows a third approach using a maleidimide reaction to conjugate the antibody with GC7 using a cleavable homofunctional crosslinker, DTME. In each aforementioned case, the GC7-based ADCs were evaluated first in vitro in cell cultures, and then in vivo using xenograft mouse models derived from eIF5A positive FG, 779E, Panc-1 and BXPC-3 pancreatic cancer cell lines purchased from ATCC, and their respective stable shRNA mediated eIF5A knockdown derivatives.

The following examples further illustrate preparation methods of the GC7-based ADC:

The following is an example preparation of GC7-mAb-DYLIGHT 550 NHS ADCs using EDC/NHS conjugation chemistry as illustrated in FIG. 3.

Briefly, the GC7 functional group (guanidine group) is protected using a modified version of the camphorquinone-10-sulfonic acid modification method or the 1,2 cyclohexadione modification method. The reaction was kept under nitrogen or argon gas for 24 hours. The protection modification was verified spectrophotometrically using the Thymol-Hypobromite reagent assay. The DYLIGHT 550 NHS fluorescence molecule is conjugated to CEA antibody and Cetuximab antibody using the standard THERMOSCI conjugation protocol for DYLIGHT fluorescent dyes. For the Cetuximab antibody, the average DAR was calculated to be 5.1, while the average DAR for the CEA antibody was 3.4. DAR. The average DAR can be determined by various conventional means such as UV spectroscopy, mass spectroscopy, ELISA assay, radiometric methods, hydrophobic interaction chromatography (HIC), electrophoresis and HPLC. To generate the GC7-mAb-DYLIGHT 550 NHS ADC, the EDC (Carbodiimide crosslinker) coupling reaction is used to conjugate/link the carboxylic acid group (—COOH) of the antibody to the primary amine group (—NH2) of the GC7, forming an amide (peptide) bond that is stable at physiological pH, and that can be cleaved during breakdown in the lysosome. The advantages of this approach is that the EDC crosslinker is not added to the final product (zero-length crosslinker), as it is used merely as an intermediate. Furthermore, using the C-terminal end rather than the N-terminus end of the antibody for conjugation, prevents the use of the primary amines found on the antigen binding sites of the antibody; thus preserving the binding ability of the antibody.

The GC7 modification is reversed by treating the ADC with 0.5M hydroxylamine buffer at pH 7.0, or by buffer exchanging the borate buffer with sodium phosphate buffer pH 7, when using the 1,2 cyclohexadione modification method. The ADC is then purified using gel exclusion chromatography. The drug load is determined via mass spectrometry, and the antibody concentration in the final ADC is determined by Bradford assay.

The following is an example preparation of GC7 mAb-SPDP-DYLIGHT 550 NHS ADC using pyridyl disulfide conjugation chemistry as illustrated in FIG. 4.

Briefly, first GC7 functional group (guanidine group), is protected using the protocol as described for FIG. 3. Second, the antibody is conjugated to DYLIGHT 550 NHS fluorescence molecule using the standard ThermoSci conjugation protocol for the DYLIGHT fluorescent dyes. DAR (Drug to Antibody ratio) was determined using standard calculations described in the protocol. The DAR (drug-to-antibody ratio) or drug loading, indicating the number of drug molecules conjugated per antibody, may be from 1 to 8. Compositions, batches, and/or formulations of a plurality of antibody-drug conjugates may be characterized by an average DAR. For Cetuximab antibody, the average DAR was calculated to be 5.1, while the average DAR for CEA antibody was 3.4. DAR. The average DAR can be determined by various conventional means such as UV spectroscopy, mass spectroscopy, ELISA assay, radiometric methods, hydrophobic interaction chromatography (HIC), electrophoresis and HPLC.

To generate the GC7-mAb-SPDP-DYLIGHT 550 NHS ADC, pyridyl disulfide reaction is used to conjugate between sulfhydryl groups (—SH) from the antibody and the primary amino group from GC7, using the SPDP (N-succinimidyl 3-(2-pyridyldithio) propionate) crosslinker; an insoluble heterobifunctional cleavable crosslinker. Prior to conjugation, the disulfide bonds at the hinge region of the antibody are reduced to yield free sulfhydryls. On one end of SPDP, the reactive moiety consisting of an N-hydroxysuccinimide (NHS) ester, reacts with the primary amine of GC7, while the other end of SPDP, pyridinyldisulfide reacts with the antibody's free sulhydryls to yield a reversible disulfide bond. The resulting disulfide bond is cleavable by endogenous glutathione, an oxidizing agent, when internalized by the tumor cell. In this approach, the antigen binding sites of the antibody are left untouched by utilizing the hinge region for bioconjugation.

Fourth, The GC7 modification is reversed by treating the ADC with 0.5M hydroxylamine buffer at pH 7.0, or by buffer exchanging the borate buffer with sodium phosphate buffer pH 7, when using the 1,2 cyclohexadione modification method. The ADC is then purified using gel exclusion chromatography. Fifth, the drug load is determined via mass spectrometry, and the antibody concentration in the final ADC is determined by Bradford assay.

The following is an example preparation of GC7-mAb-STME-DYLIGHT 550 NHS ADCs using maleimide conjugation chemistry as illustrated in FIG. 5.

Briefly, the GC7 functional group (guanidine group) is protected as described in Example 1, and the DYLIGHT 550 NHS is conjugated to CEA antibody and Cetuximab antibody as described in Example 1. For the Cetuximab antibody, the average DAR was calculated to be 5.1, while the average DAR for the CEA antibody was 3.4. DAR. The average DAR can be determined by various conventional means such as UV spectroscopy, mass spectroscopy, ELISA assay, radiometric methods, hydrophobic interaction chromatography (HIC), electrophoresis and HPLC.

To generate the GC7-mAb-STME-DYLIGHT 550 NHS ADCs, maleimide reaction is used to conjugate between sulfhydryl groups (—SH) from the antibody and GC7 (FIG. 5). Prior to conjugation, the GC7 primary amine groups are modified to sulfhydryl groups by thiolation (sulfhydryl addition) using Traut's reagent (2-iminothiolane), and the disulfide bonds at the hinge region of the antibody are reduced to yield free sulfhydryls. DTME (Dithiobismaleimidoethane) crosslinker with maleimide on both ends (homobifunctional cross linker), reacts with the sulfhydryl groups of the antibody on one end and of the drug on the other end to link them. The disulfide bond of DTME is cleavable by endogenous glutathione, an oxidizing agent, when internalized by the tumor cell. In this approach, the antigen binding sites of the antibody are also left untouched by utilizing the hinge region for bioconjugation.

The GC7 modification is reversed by treating the ADC with 0.5M hydroxylamine buffer at pH 7.0, or by buffer exchanging the borate buffer with sodium phosphate buffer pH 7, when using the 1,2 cyclohexadione modification method. The ADC is then purified using gel exclusion chromatography. The drug load is determined via mass spectrometry, and the antibody concentration in the final ADC is determined by Bradford assay.

The following is an example preparation of the cell viability assays used to demonstrate cell viability and lethality in FIG. 6, FIG. 7, FIG. 8, and FIG. 9.

PDAC cell lines BxPC-3, FG, Panc-1, and 779E were obtained from American Type Culture Collection and were grown according to standard protocols. Per western blot analysis all cell lines are positive for eIF5A. Cell lines BxPC-3 (high) and 779E (low) express CEA, while PG and Panc-1 do not express CEA. All cell lines express EGFR (BxPc-3 and Panc-1 (high), PG and 779E (medium)). Panc-1 cell line is KRAS mutated, Cetuximab sensitive and Gemcitabine (leading chemotherapy drug for PDAC) resistant. FG cell line is Cetuximab sensitive in-vivo/resistant in-vitro, and Gemcitabine sensitive. There is currently no information on the KRAS phenotype of PG cell line. BxPc-3 cell line is KRAS wild-type, Cetuximab and Gemcitabine resistant. There is no current information on drug resistance and sensitivity of 779E cell line. 779E cell line is KRAS mutated.

After purification via gel chromatography, the cytotoxicity effect of the drug on the eIF5A positive tumor cell compared to eIF5A negative cells is determined by measuring the loss of fluorescence signal of the GFP tagged tumor cells after administration of the ADC in vitro in the cell media.

The effects of the 6 ADCs on tumor cell growth were assessed using Crystal Violet staining assay. In a well plate, cells were seeded at a concentration of 2000 cells on day one, and allowed to grow for 3 days. Each well was subject to a corresponding treatment listed in FIGS. 6a, 7a, 8a, and 9a.

FIGS. 6b, 7b, 8b, and 9b show raw data in form of Crystal Violet stains for various controls and drug treatments in various cell lines, and the raw data is represented in graphic form in FIGS. 6c, 7c, 8c, and 9c. Treatment groups correspond to the each well plate. The "no drug" represents the molarity in microns (e.g., GC7 25 means 25 uM of GC7). The following are the reagents used in the assays: Dylight 550 NHS—fluorescent dye; CET—Cetuximab, CEA—Carcinoembryonic antigen. SPDP, DTME and EDC are three crosslinkers used to attach drug GC7 to antibody-dye conjugate. Final conjugate comprises of antibody, dye, crosslinker and GC7. In general, the ADCs showed similar cytotoxicity on wildtype and drug resistant cell lines. ADCs conjugated with STME had the least cytotoxic effects while ADCs conjugated with SPDP or EDC had the most cytotoxic effects.

Figure 10:
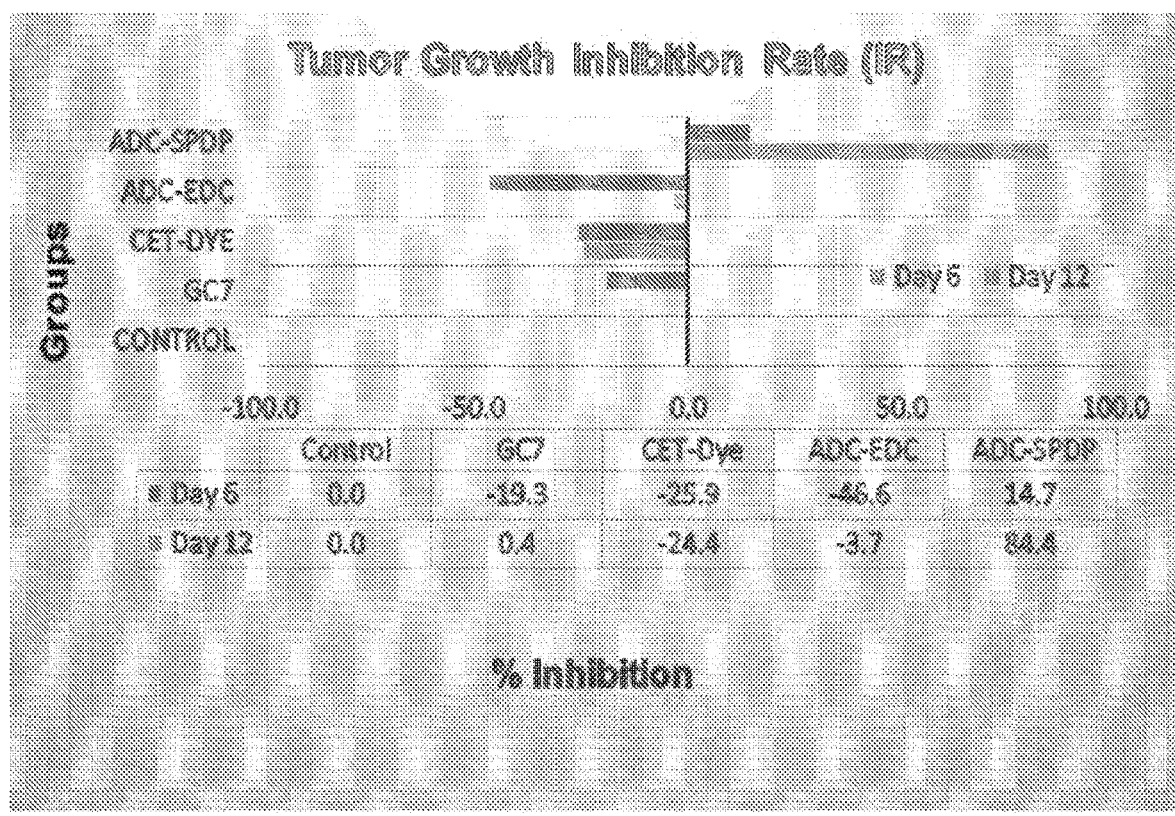
FIG. 10 shows the results of an in vivo efficacy assay of the present invention in nude mice with bi-lateral subcutaneous tumors derived from 779E cells.
Figure 11:
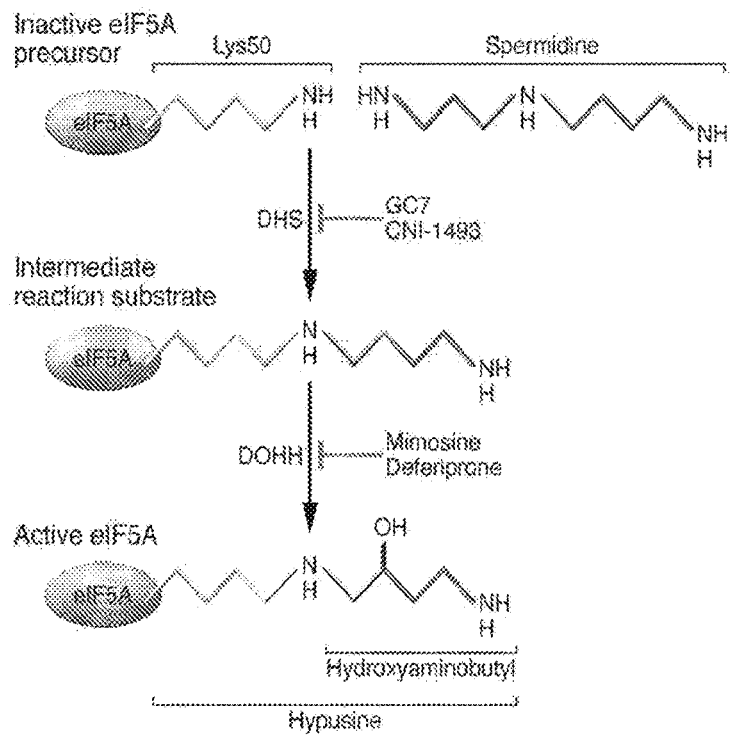
FIG. 11 shows a graphic depiction of the eIF5A hypusination pathway.

The following is an exemplary protocol and results for in-vivo analysis of ADCs cytotoxic effect in subcutaneous mouse model as illustrated in FIG. 10.

After purification via gel chromatography, where the cytotoxicity effect of the drug on the eIF5A positive tumor cell compared to eIF5A negative cells was determined by measuring the loss of fluorescence signal of the GFP tagged tumor cells after administration of the ADC in vivo via tail vein injection in mice using an IVIS Spectrum in vivo imaging system. As shown in the graph in FIG. 10, GC7-Cetuximab-EDC-DYLIGHT 550 NHS resulted in −3.7% tumor growth inhibition after 12 days, GC7-Cetuximab-SPDP-DYLIGHT 550 NHS resulted in 84.4% tumor growth inhibition, compared to 0.4% with GC7 alone.

The cancer-cell specific binding efficiency of the ADCs was determined by confirming the co-localization of the red fluorescence from the ADCs DYLIGHT 550 NHS dye, with the green fluorescence of the Green Fluorescent Protein (GFP) transfected tumor cells. Absence of co-localization as control, was determined with cell lines previously treated with corresponding antibodies to block antigen binding sites.

Embodiments of the product forms of the current invention may be, in various dosage forms. Dosage forms can be prepared for mucosal (e.g., nasal, sublingual, vaginal, buccal, or rectal), parenteral (e.g., sub-cutaneous, intravenous, intramuscular, or intraarterial injection, either bolus or infusion), oral, or transdermal administration to a subject. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosa! administration to a subject, including suspensions (e.g., aqueous or non-aqueous liquid suspensions, oil-in-water emulsions, or a water-in-oil liquid emulsions), solutions, and elixirs; liquid dosage forms suitable for parenteral administration to a subject; and sterile solids (e.g., crystal-line or amorphous solids) that can be reconstituted to provide liquid dosage forms suitable for parenteral administration to a subject.

Injectable (e.g., intravenous) compositions can comprise a solution of the antibody or antibody-targeted composition suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc. In some embodiments, the composition can be formulated in a kit for intravenous administration.

The formulations of various embodiments of the current invention comprise an active ingredient in association with a pharmaceutically acceptable carrier therefor and optionally other therapeutic ingredient(s). The carriers) must be "acceptable" in the sense of being compatible with the other ingredients of the formulations and not deleterious to the recipient thereof.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration.

The formulations of targeted compositions can be presented in unit-dose or multi-dose sealed containers, such as ampoules and vials.

The formulations may conveniently be presented in mint dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

An GC7 conjugate also be formulated to provide more than one active compound, e.g., additional chemotherapeutic or cytotoxic agents, cytokines, or growth inhibitory agents. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)) car polylactides). The conjugates can be entrapped in a nanoparticle prepared, for example, by coacervation techniques or by interfacial polymerization, for example, hydroxymethylcellulose or gelatin microcapsules and poly-(methylmethacylate) micro-capsules, respectively, in colloidal drug delivery systems (for example, liposomes, albumin microspheres, microemulsions, nano-particles and nanocapsules) or in macroemulsions.

The pharmacologically active compounds of the disclosure are useful in the manufacture of pharmaceutical compositions comprising an effective amount thereof in conjunction or admixture with the excipients or carriers suitable for either enteral or parenteral application. Preferred are tablets and gelatin capsules comprising the active ingredient together with one or more of the following: (a) diluents, such as lactose, dextrose, sucrose, marmitol, sorbitol, cellulose, glycine and the like; (b) lubricants, such as silica, talcum, stearic acid, its magnesium or calcium salt, polyethyleneglycol and the like; for tablets also; (c) binders, such as magnesium aluminum silicate, starch paste, gelatin, tragacanth, methylcellulose, sodium carboxymethyl-cellulose or 30 polyvinylpyrrolidone and the like; and, if desired, (d) disintegrants, such as effervescent mixtures and the like; and (e) absorbents, colorants, flavors, and sweeteners and the like.

Embodiments of the current invention may be formulated by a pharmaceutically acceptable carrier. Said pharmaceutical compositions may be sterilized and/or contain adjuvants, such as preserving, stabilizing, wetting or emulsifying agents, solution promoters, salts for regulating the osmotic pressure, and/or buffers. In addition, they may also contain other therapeutically valuable substances. Said compositions are prepared according to conventional mixing, granulating, or coating methods, respectively, and contain a determined amount the active ingredient.

The invention claimed is:

1. A compound for detecting and treating cancer cells, such compound comprising:

n(m(I)-L)-Ab-(L-(D)m)n, wherein Ab represents a molecule from the group consisting of an antibody, a peptide, a polypeptide, a protein, and an antigen binding fragment;
wherein D represents a drug moiety;
wherein I represents an imaging agent;
wherein L represents a linker:
wherein m represents an integer in the range of 1 to 8;
wherein n represents an integer in the range of 1 to 10; and
wherein the drug moiety is a form of N1-guanyl-1,7-diaminoheptane (GC7) linked to the linker by the primary amine group at the 7-position of GC7.

2. The compound of claim 1, wherein the form of GC7 is a salt form.

3. The compound of claim 1, wherein said linker is a carbodiimide crosslinker, a succinimidyl-3-(2-pridyldithio)propionate crosslinker or a dithiobismaleimidoethane crosslinker.

4. The compound of claim 1, wherein Ab is an antibody or antibody fragment able to bind specifically to epidermal growth factor receptor (EGFR) or to carcinoembryonic antigen (CEA).

5. A pharmaceutical composition comprising the compound of claim 1 and a pharmaceutically acceptable carrier, vesicle or excipient.

* * * * *